(12) United States Patent
Meehan et al.

(10) Patent No.: US 8,563,013 B2
(45) Date of Patent: Oct. 22, 2013

(54) SYSTEMS AND METHODS FOR DELIVERING A FLUID DRUG

(75) Inventors: Anthony Meehan, Newtown, PA (US); Glenn R. Booma, Natick, MA (US); Gerd Schmieta, Boston, MA (US); David L. Weissburg, Lexington, MA (US); Jonathan Belfort, Cambridge, MA (US); Mekayla Beaver, Boulder, CO (US); Gary A. Meade, Ewing, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 102 days.

(21) Appl. No.: 12/594,785

(22) PCT Filed: Mar. 27, 2008

(86) PCT No.: PCT/US2008/058506
§ 371 (c)(1),
(2), (4) Date: Apr. 20, 2010

(87) PCT Pub. No.: WO2008/124330
PCT Pub. Date: Oct. 16, 2008

(65) Prior Publication Data
US 2010/0240757 A1 Sep. 23, 2010

Related U.S. Application Data

(60) Provisional application No. 60/910,466, filed on Apr. 6, 2007.

(51) Int. Cl.
*A61K 9/00* (2006.01)
(52) U.S. Cl.
USPC .......................................................... 424/400
(58) Field of Classification Search
None
See application file for complete search history.

(56) References Cited

U.S. PATENT DOCUMENTS

| | | | | |
|---|---|---|---|---|
| 3,921,860 A | * | 11/1975 | Zackheim | 222/207 |
| 4,147,189 A | * | 4/1979 | Wippermann | 141/18 |
| 4,607,762 A | * | 8/1986 | Zulauf et al. | 222/48 |
| 5,330,081 A | * | 7/1994 | Davenport | 222/207 |
| 6,102,254 A | * | 8/2000 | Ross | 222/192 |
| 6,253,967 B1 | | 7/2001 | Sperna Weiland | |
| 6,330,960 B1 | | 12/2001 | Faughey et al. | |
| 7,097,071 B2 | | 8/2006 | Anderson et al. | |
| 7,160,913 B2 | | 1/2007 | Schneider | |
| 2004/0007555 A1 | * | 1/2004 | Steele, IV et al. | 215/228 |
| 2005/0070608 A1 | * | 3/2005 | Remenar et al. | 514/567 |
| 2005/0203185 A1 | | 9/2005 | Remener et al. | |
| 2006/0016835 A1 | | 1/2006 | Perry | |
| 2010/0213211 A1 | * | 8/2010 | Whaling et al. | 222/111 |

FOREIGN PATENT DOCUMENTS

| | | |
|---|---|---|
| AU | 731320 | 3/2001 |
| DE | 1075967 | 2/1960 |
| DE | 19603707 | 8/1997 |
| JP | 2002-531338 | 9/2002 |
| JP | 2007-504143 | 3/2007 |
| WO | WO 00/33969 | 6/2000 |
| WO | WO 2005/023185 | 3/2005 |

OTHER PUBLICATIONS

Tury et al. Deceleration of light-induced changes of selected pharmacons by means of light screening films. Journal of Photochemistry and Photobiology A: Chemistry 111(1-3):171-179, 1997.*
International Search Report for PCT/US2008/058506 dated Jun. 4, 2009.
European Search Report Re: EP 08744502.9 dated May 17, 2011.

* cited by examiner

*Primary Examiner* — Robert A Wax
*Assistant Examiner* — Olga V Tcherkasskaya
(74) *Attorney, Agent, or Firm* — Kiera K. Mathey

(57) ABSTRACT

Devices and methods for distributing a fluid, e.g., a fluid drug, are disclosed. Fluid-drug distribution can be advantageously utilized to help patients suffering from a disorder that affect fine motor skill usage, e.g., Parkinson's Disease. Some aspects are directed to dosing containers that are adapted to distribute one or more selected dosages of fluid from the container. In some instances, the containers are adapted to be operable by patients with hindered fingertip motor control to help dispense a fluid-drug, such as a fluid including carbidopa and levodopa. Other aspects are directed to a kit for distributing a fluid drug that can be stored with a longer shelf life in solid form. Also discussed herein are methods for distributing a fluid drug for treating a disorder such as Parkinson's Disease.

16 Claims, 14 Drawing Sheets

SYSTEMS AND METHODS FOR DELIVERING A FLUID DRUG

CROSS REFERENCE TO RELATED APPLICATIONS

This application is the national stage of PCT Application No. PCT/US2008/058506, filed Mar. 27, 2008, which claims priority from U.S. Provisional Application No. 60/910,466, filed Apr. 6, 2007, the entire disclosures of which are hereby incorporated in their entirety.

FIELD OF THE INVENTION

The present invention relates to delivering a fluid drug, and more particularly to delivering a fluid drug to patients with hindered motor function.

BACKGROUND OF THE INVENTION

Parkinson's disease (herein "PD") is a degenerative disorder of the central nervous system, which can impair the motor skills and speech of the afflicted. PD is characterized by muscle rigidity, shaking, and a slowing of movement (bradykinesia), and can lead to a loss of physical movement (akinesia). The physical manifestations are typically caused by damage to the brain's neurons, leading to a decrease in the production of dopamine. PD is both chronic and progressive. In the late stages of the disease, complications such as choking, pneumonia, and falls that can lead to death are possible.

No cure for PD is currently known. Thus, treatment options are generally directed at attempting to alleviate the symptoms of the disease. One treatment regime includes the use of levodopa to alleviate symptoms such as slowness, stiffness, and tremors. Levodopa is an aromatic amino acid, which can be modified by brain enzymes to produce dopamine. The presence of aromatic L-amino acid decarboxylase in the blood tends to break down the levodopa before the levodopa reaches the brain. Thus, an aromatic amino acid decarboxylation inhibitor such as carbidopa can be included to hinder levodopa degradation. The combination of levodopa and carbidopa are administered in tablet form to patients.

Though the combination of levodopa and carbidopa can provide some relief to PD patients, problems persist in the delivery of the drug. For patients with decreased motor function skills, the handling of tablets can be difficult and troublesome. As well, the tracking of the medicine dosages can require substantial effort. Even the swallowing of the tablets can be problematic for some PD sufferers. Difficulties with the delivery of drugs can hinder patients from properly following a prescribed treatment regime, which can further aggravate the impact of the disease.

Accordingly, a need exists for improved methods and devices that improve the delivery of formulations such as carbidopa and levodopa to patients with decreased motor function.

SUMMARY OF THE INVENTION

Some aspects of the invention are directed to devices and methods for distributing a fluid drug, such as a fluid formulation of carbidopa and levodopa. In particular, some aspects include devices and methods which can aid in the delivery of such fluid formulations to patients with impaired motor skills, such as persons suffering from PD.

One exemplary embodiment is directed to a dosing container. The dosing container can be adapted to be operated by a person with limited hand motor skills. Such a container can include a reservoir for holding a fluid, such as a fluid drug (e.g., fluid including carbidopa and levodopa). The reservoir can be adapted hinder exposure of a fluid contained therein to portions of a light spectrum. For example, light capable of inducing degradation in either or both of carbidopa and levodopa, when dispersed in a fluid, can be preferably hindered from an internal region of the reservoir. The container can also include a cup which can be coupled to the reservoir. The cup can be adapted to hold one or more selected dosages of fluid. A rotatable cap can be coupled to the cup, and can be adapted to rotate to one or more selected positions. The cap can be coupled to rotate relative to the cup, or the cup can rotate with the cap. Each of the selected positions can be for distributing an amount of fluid corresponding with one of the selected dosages. The rotatable cap can also be adapted to be hand-grippable and rotatable by a person with hindered fingertip motor skills. The dosing container can be adapted to fill a cup substantially with a selected dosage of fluid when the dosing container is squeezed by a user.

The dosing container can include additional features such as a straw adapted to be fitted to a portion of the cup (e.g., attached to the cup at a position away from the centerline axis of the cup). The straw can be used to draw fluid from the reservoir to the cup. The straw can have an inner diameter sized to provide selected dosages of fluid within an error of about 10%. The reservoir of the dosing container can include at least one indentation for orienting the container in a particular direction relative to a person using the dosing container. The container can also include a flip lid, which can be used to cover an opening in the rotatable cap. Optionally, the container can be adapted such that the selected positions of the rotatable cap are determined such that the flip lid opens in a direction away from a user when the container is oriented in a particular direction. The reservoir of the container can include a threaded portion for attaching to the cup, the threaded portion adapted to accept a standard child-proof fitting. Furthermore, the cup and rotatable cap can be adapted to hinder decoupling after the cup and rotatable cap are coupled together.

A dosing container can include a sleeve, which can be adapted to couple and rotate in sync with the rotatable top of the container. The sleeve can include one or more openings along its length. Each opening can correspond with a selected dosage. The sleeve can be adapted to fit over a post structure of the cup to form a slot for guiding fluid from the reservoir into the cup. The post can include a structure such as a groove which can form part of a boundary for the slot. The slot can be configured to run along the post, and can be adapted not pass through the post.

Another exemplary embodiment is directed to a kit for treating Parkinson's Disease. The kit can include a container adapted to deliver at least one selected amount of fluid. The container can be any particular dosage container. For example, a dosing container can be a container as disclosed in the present application, including one or more the features disclosed herein. The kit can further include a concentrated carbidopa formulation and a concentrated levodopa formulation. The formulations can be in fluid or solid (e.g., powdered) form, and can be separately packaged or packaged together. The formulations can also be adapted to provide one or more dosages of fluid-drug for treating a patient with Parkinson's Disease when the formulations are dispersed in water. In one example, the concentrated carbidopa and levodopa formulations are is a ratio of about 1:4. In a related embodiment, a kit can include a plurality of containers, concentrated carbidopa formulations, and concentrated levodopa formulations. The kit can have equal numbers of each formulation and a container.

Another exemplary embodiment is drawn to a method of treating Parkinson's Disease. The method includes providing one or more powdered formulations, which can include carbidopa and levodopa. The powdered formulation(s) can be dispersed in water, with the dispersion contained in a dosage container adapted to provide selected dosages of the dispersed powdered formulations. Dosage containers for use with the method can include containers adapted to be operable by a patient having hindered fingertip motor skills. In some instances, the dosage container can be locked after the container is closed with the dispersed powdered formulation(s), which can hinder tampering. The dosage container can be squeezed while the container is oriented in an upright position to displace a selected dosage of dispersed powder formulation from a fluid reservoir of the container to a cup.

BRIEF DESCRIPTION OF THE DRAWINGS

The invention will be more fully understood from the following detailed description taken in conjunction with the accompanying drawings (not necessarily to scale), in which.

DETAILED DESCRIPTION OF EMBODIMENTS OF THE INVENTION

Figure 1A:
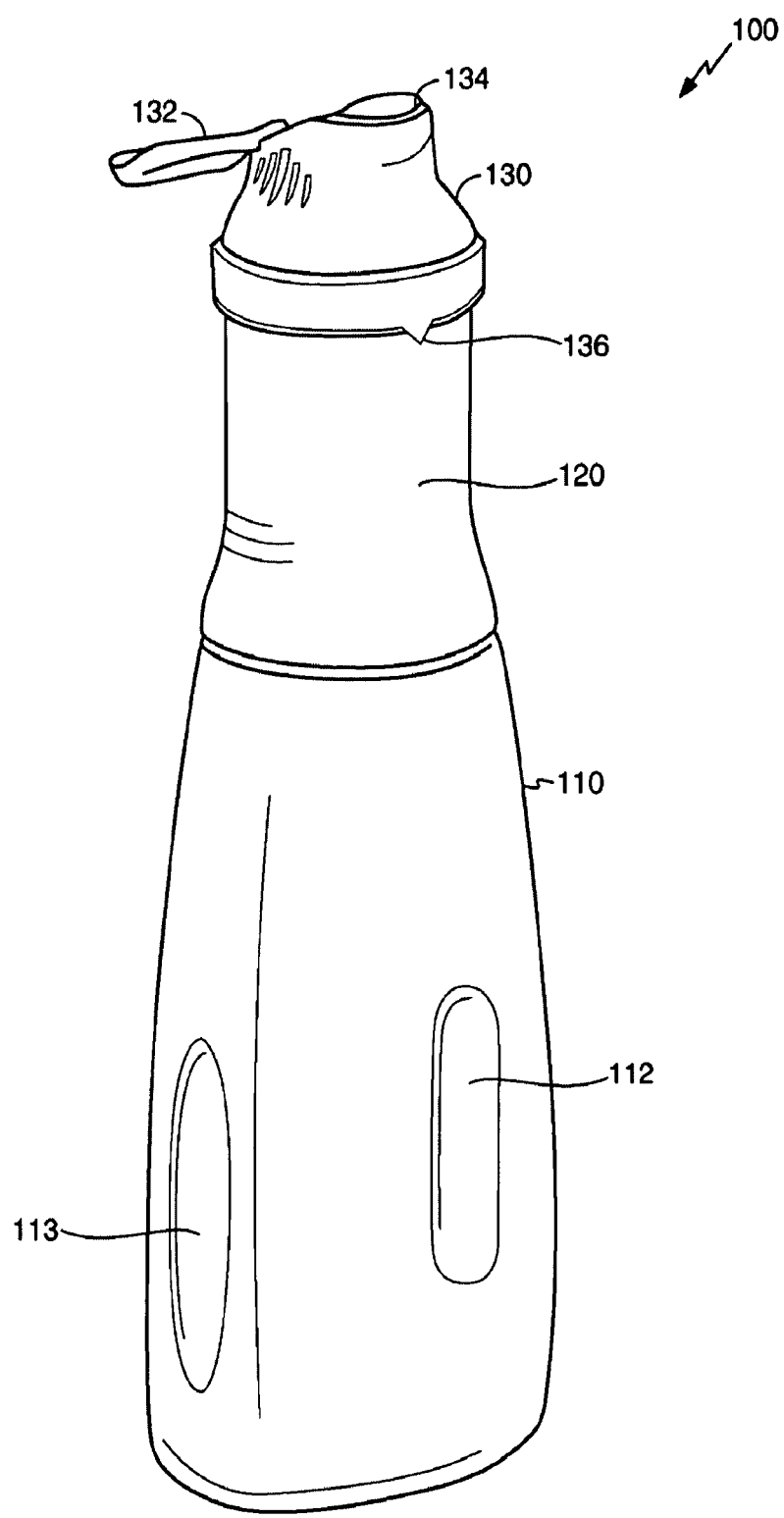
FIG. 1A presents a schematic of a perspective view of a dosing container consistent with embodiments of the present invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments, and that the scope of the present invention is defined solely by the claims. The features illustrated or described in connection with one exemplary embodiment may be combined with the features of other embodiments. Such modifications and variations are intended to be included within the scope of the present invention.

For example, some embodiments of the present invention are directed to various aspects of delivery of a fluid drug. Such embodiments can be particularly useful in aiding persons afflicted with of Parkinson's Disease (PD) in obtaining a fluid formulation of levodopa and carbidopa in an appropriate dosage form and amount. It is understood, however, that such embodiments can be utilized in a variety of other contexts such as for other person's suffering from decreased motor function, or for PD patients desiring distribution of another fluid drug formulation.

Dosing Containers for Person's with Hindered Motor Skills

Some embodiments of the invention are directed toward a dosing container. For the purposes of the present application, dosing containers include fluid containers that are capable of delivering one or more selected amounts of fluid from a larger reservoir. The selected amount can typically be metered by the container without requiring the user to actively adjust the amount of fluid dispensed into a conduit. Though some embodiments herein can utilize a variety of dosing containers, including ones known to those skilled in the art, particular embodiments utilize a dosing container which can be operated by a person with hindered motor skills. For example, bottles that distribute a designated amount of fluid for use are known. These bottles, however, generally utilize features that require the use of fine fingertip motor skills to effectively distribute the given amount of fluid, e.g., twisting of a thin knob to choose a particular setting for the bottle to distribute the corresponding amount of fluid, and manual orientation of the bottle into a particular position to effect dispensing of a dose. Accordingly, such bottles can be inappropriate for use by patients suffering from PD or other motor skill deficiencies that hinder the usage of existing dosing containers.

Thus, some exemplary embodiments are directed to a dosing container, which can be operated by a person with limited hand motor skills. The dosing container includes a reservoir for holding a supply of fluid to be distributed. The container can also include a rotatable cap which is adapted to be coupled to the reservoir, and which can generally rotate relative to the reservoir. The rotatable cap can be adapted to rotate to one or more selected positions, each position corresponding with a selected amount of fluid to be distributed from the container. Furthermore, the rotatable cap can be adapted to be hand-grippable and rotated by a person with hindered fingertip motor skills.

Dosing containers consistent with some embodiments of the invention described herein can be used to hold any compatible fluid formulation, including fluid drug formulations. In one example, a fluid drug formulation includes one or more of carbidopa and levodopa dispersed in a medium such as water. The carbidopa and levodopa can be any ratio appropriate for use with a patient such as a person afflicted with PD. Some such fluid formulations are generally described in U.S. Patent Application Publication No. US 2005/0203185 A1, bearing Ser. No. 11/083,168; and U.S. Patent Application Publication No. US 2005/0070608 A1, bearing Ser. No.

10/926,702. Of course, other fluid formulations can also be utilized with a dosing container, including fluids that do not include a drug.

An exemplary dosing container is depicted in FIGS. 1A-6B. The depicted dosing container 100 can have a tapered shape, which has a generally smaller cross-section near the top and generally larger cross section at the bottom. Though use of such a tapered shape is not necessary, such a design can provide container stability while facilitating usage with persons having small and/or weak hands. The dosing container 100 includes a reservoir 110 and a rotatable cap 130. A cup portion 120 can be coupled to the reservoir 110, e.g., such that the cup portion 120 stays fixed relative to the reservoir 110. The rotatable cap 130 can include an indicator, e.g., a pointing structure 136 or some other marking or structure, that is used to provide a way of determining the relative rotational position of the cap 130 relative to the cup 120. Thus, when a user rotates a rotatable cap, the position of the cap can correspond with one or more positions that are indicative of the device being configured to dispense a selected amount of fluid. In some embodiments, the dosing container can be configured such that the rotatable cap can be selectively rotated into a discrete number of stable positions that correspond with doses, and/or a position that effectively hinders distribution of fluid from the container (e.g., prevents fluid from flowing into a cup portion).

Usage of an exemplary dosing container to deliver a dosage of fluid is described with reference to FIGS. 1A and 1B. In general, a dosing container can be oriented in an upright position, with the container optionally resting on a flat surface as depicted in FIG. 1A. The rotatable cap 130 can be rotated into a position corresponding with a desired dosage of fluid to be distributed from the container. The reservoir portion 110 can be squeezed, causing fluid in the reservoir 110 to be displaced into a cup region 120. In particular, the amount of fluid displaced into the cup 120 can be dependent upon the position of the rotated cap 130, with the container adapted to hinder over or under distribution of the amount of fluid desired. After distribution of the selected amount of fluid into the cup 120, selected amount can be removed from the cup 120, e.g., poured out of the container into another container or into the mouth of a user.

It is understood that the aforementioned description is one way that a dosing container can be operated, and that other dosing containers, consistent with some embodiments discussed herein, can operate in a different fashion. As well, the mechanics of how fluid is distributed from a reservoir into a cup can vary, with some details described herein consistent with some embodiments.

The total amount of fluid that can be held in a dosage container, and the selected amounts of fluid that can be selectively distributed by the container (e.g., by rotating the cap to a selected position and squeezing the reservoir), can be varied depending upon the desired usage of the dosing container. In some embodiments, including the embodiments consistent with FIGS. 1A-6C, the dosing container can hold a total volume of fluid at least about 200 mLs or at least about 300 mLs in a reservoir. The reservoir can be designed to include an additional volume of headspace, e.g., about 50 mLs, beyond the volume of fluid intended to be held in the reservoir, to facilitate mixing of fluid within the container. In addition, or alternatively, the container can be adapted to have a rotatable cap that can be rotated to any one of five selected positions. One of the positions can be an OFF position that corresponds with not allowing fluid to be distributed out of the container reservoir. The remaining four positions can correspond with distributing amounts of ¼, ½, ¾, and one full dosage of a selected volume of fluid. In general, a full dosage of a selected volume can be any volume, but in some embodiments is in the range of about 10 mLs to about 50 mLs; or in the range of about 25 mLs to about 35 mLs; or about 25 mLs. In a particular example, a given volume of fluid can include a mixture of carbidopa and levodopa in a ratio of 1:4, though other ratios can also be utilized. It is understood that these aforementioned amounts are merely non-limiting examples, and that any number of amounts can be utilized in an appropriately configured dosing container.

Accordingly, dimensions of the dosing container 100 are determined in part by the previously selected amounts in some embodiments. As well, the sizes of pieces such as the rotatable cap 130 can be chosen to facilitate usage by person's with hindered fingertip motor control. For example, the rotatable cap 130 can have a diameter greater than about 2 cm with a growing taper to a diameter greater than about 3 cm. As well, the height of the rotatable cap 130 can be greater than about 2 cm. These dimensions are exemplary, and other dimension can also be utilized.

Figure 1B:
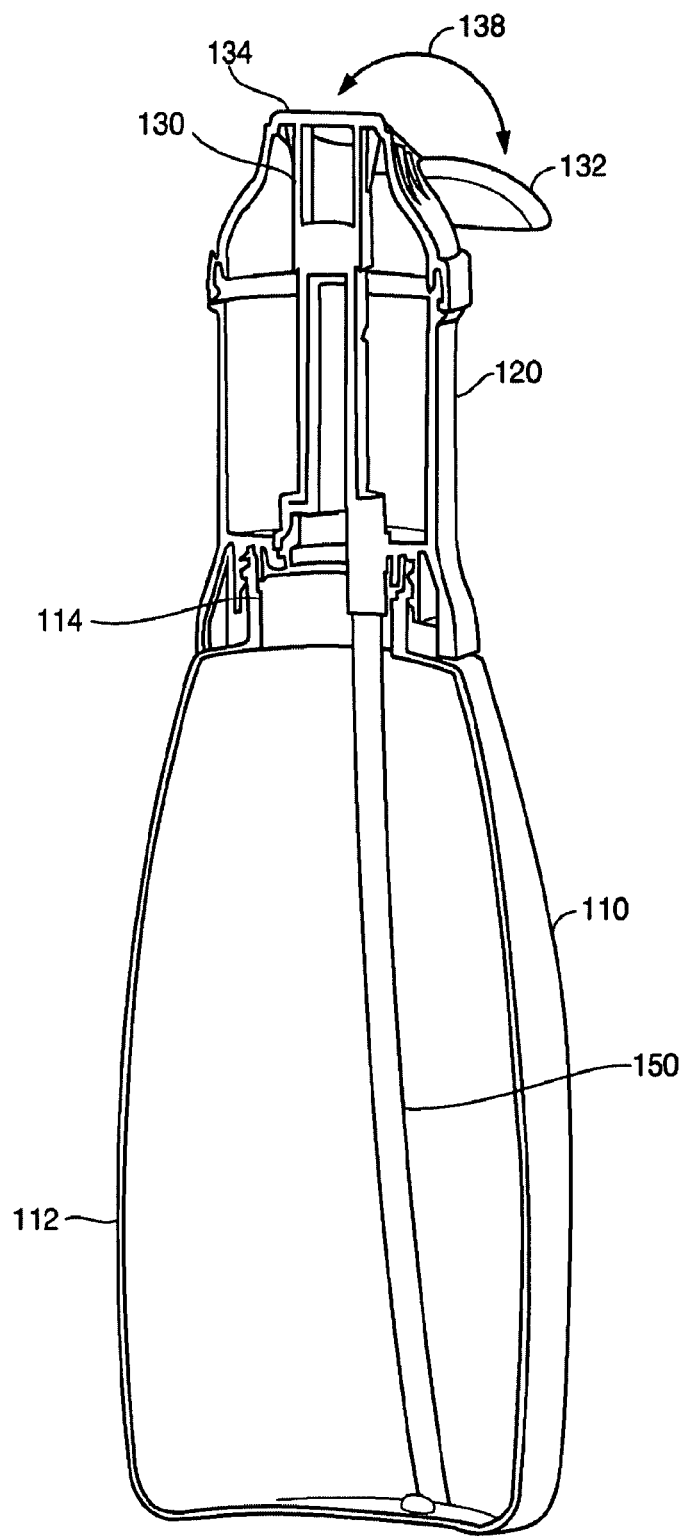
FIG. 1B presents a schematic of a cross-sectional perspective view of the dosing container shown in FIG. 1A.
Figure 2A:
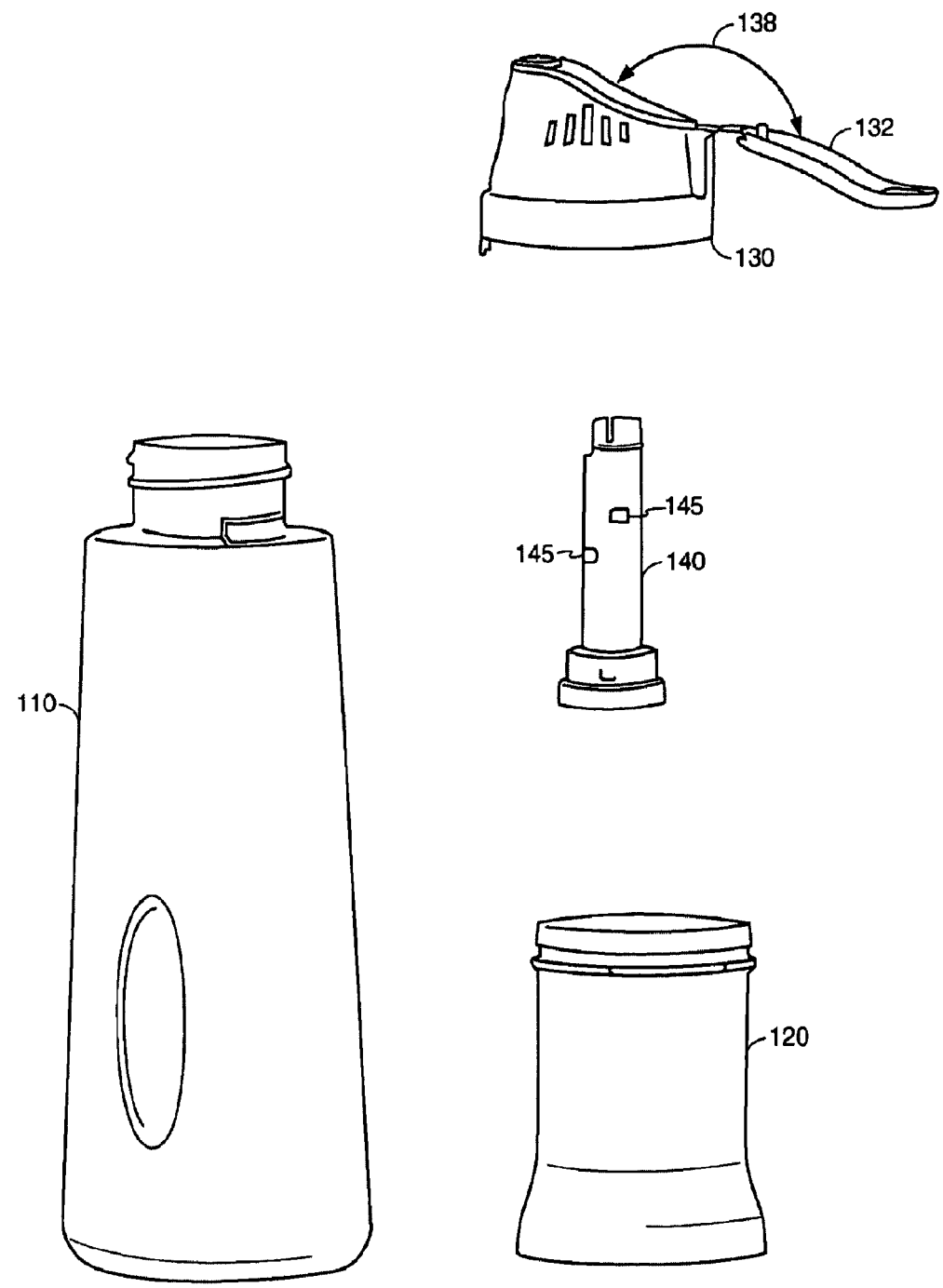
FIG. 2A presents a schematic of an exploded view of some of the pieces of the dosing container shown in FIG. 1A.
Figure 2B:
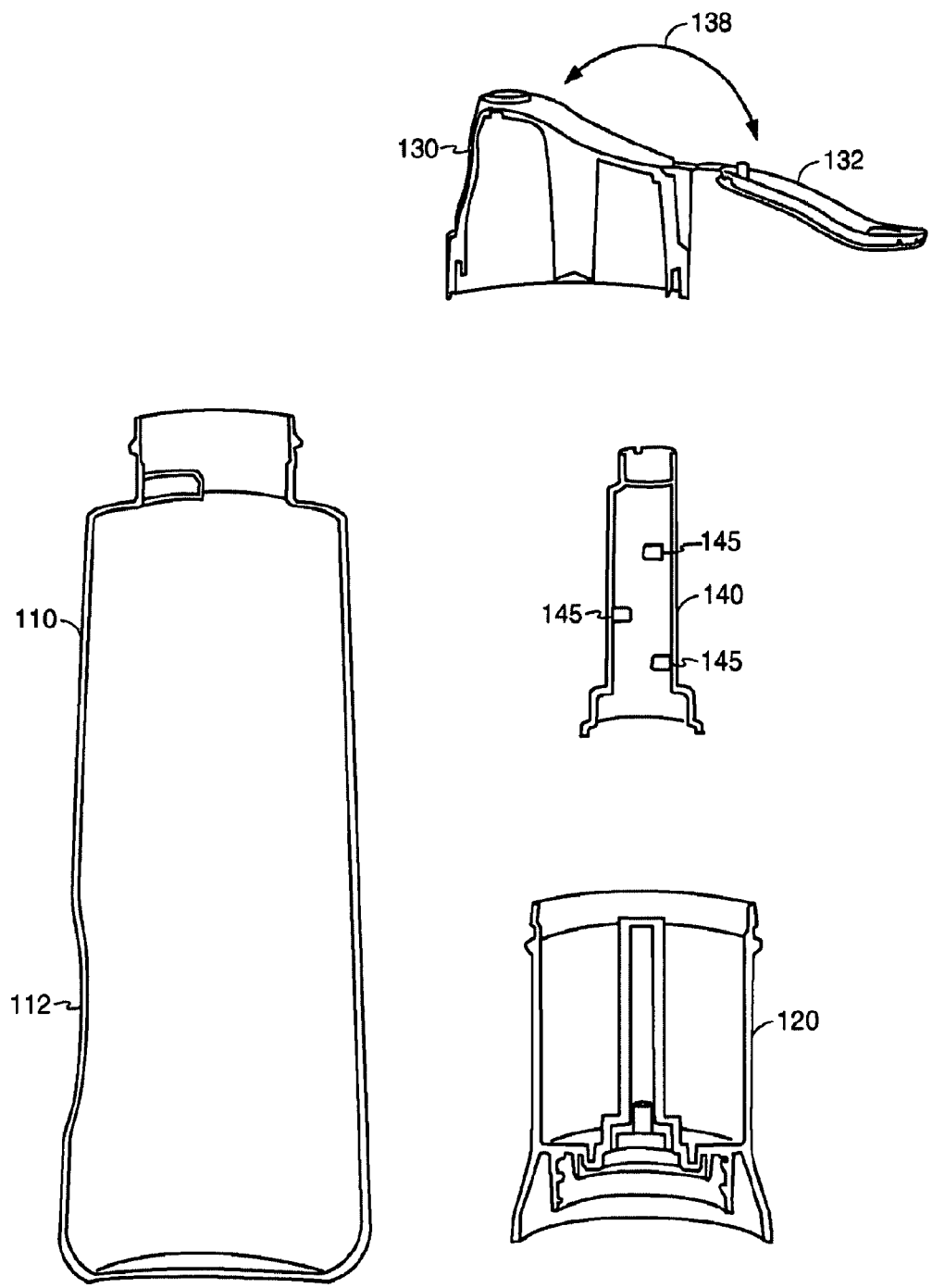
FIG. 2B presents a schematic of a cross-sectional view of the pieces of the dosing container shown in FIG. 2A.

A rotatable cap 130 of a dosing container 100 can optionally include a flip lid 132, which can be hinged to the remainder of the cap as exemplified in FIGS. 1A and 1B. When the flip lid 132 is in a closed position (e.g., the lid can be adapted to have a snap fit shut, which is optionally fluid-tight), the lid 132 covers an opening 134 that is in fluid communication with the inner volume of the cup 122. A flip lid can provide a potential advantage over a lid that requires rotation since the rotational motion of the lid can be confused with the rotation of the cap in selecting a dosage; this feature can be especially desirable when the container is intended to be used by persons with hindered fine motor function. In some instances, the flip lid 132 can have a resting open position that forms at least about a 90 degree angle relative to the flip lid 132 position when the lid 132 is closed. For example, as depicted in FIGS. 1B, 2A, and 2B, the open flip lid 132 forms an angle 136 with the remainder of the cap 130 that is much greater than 90 degrees. The angle of the opening can be greater than about 140 degrees, or even greater than about 180 degrees. By utilizing such a feature, the flip lid 132 can be removed from the opening 134 of the cap 130 sufficiently to allow a user easy access to the opening 134, which can facilitate pouring of fluid or drinking from the container 100.

As shown in FIGS. 1A, 1B, 2A, and 2B, the reservoir 110 can include some type of structure or marking, e.g., an indentation 112, which allows an orientation to be assigned to the container 100. Structures or markings can also, or alternatively, be implemented on other parts of a container to provide orientation. Though orientation of a dosing container is not a necessary feature of some embodiments, it can be associated with various advantages such as allowing the container to be oriented relative to a user to facilitate container usage. For example, the reservoir 112 shown in FIG. 1A can have an oblong footprint, which can be used with the indentation 112 to orient the container 100 when the container is used to dispense fluid, e.g., having the indentation 112 face the user when the user is operating the container. The container can be configured such that by holding the reservoir in the preferred orientation, fluid in the reservoir can be transported into the cup portion by squeezing the container. Such an orientation can be useful to a user with limited hand motor skills, positioning the container so that the container is easily squeezed along the minor-axis direction, when so configured.

In another example, positioning the container in a preferred orientation relative to a user can allow the container's rotatable cap to be positioned to facilitate fluid distribution to the user. For instance, when a flip lid 132 is included with the rotatable cap 130, as exemplified by the embodiment shown in FIGS. 1A, 1B, 2A, 2B, 4, and 6C, the container 100 can be adapted such that the open flip lid 132 does not hinder distribution of a selected fluid amount from the container 100, e.g., the flip lid 132 opens in a direction away from a user holding the container 100. With respect to FIG. 1A, the dosing container 100 can have a preferred orientation where the indentation 112 faces a user holding the container 100. In this orientation, the container 100 can be adapted such that for any one of the potential selectable rotational positions of the rotatable cap 130, the open flip lid 132 is not directly facing the user, i.e., the flip lid does not open substantially in the direction of the indentation 112. Thus, a user can drink from the opening 134 when the flip lid 132 is open without needing to rotate the entire container 100 to move the flip lid 132 out of the way of the user. Such a feature, besides lending convenience to a user, can be especially helpful to person with hindered hand motor skills.

In some embodiments, the reservoir, and/or other portions of a dosing container, can be adapted to hinder exposure of a contained fluid from portions of a light spectrum, which can be capable of degrading or rendering one or more components of a fluid ineffective. For example, a fluid formulation having carbidopa has been found to degrade when exposed to visible light with wavelengths in the range of about 400 nm to about 550 nm. This result is unexpected in that carbidopa does not appear to absorb wavelengths of light appreciably above 300 nm. Accordingly, if a container is adapted to hinder a carbidopa-containing fluid from being exposed to at least wavelengths in about the 400 nm to about 550 nm range, preservation of the carbidopa can be enhanced. As well, other embodiments can utilize other techniques, in combination or alone, which effectively reduce degradation of a carbidopa-containing fluid in the presence of visible light, such as adding a dye to the carbidopa-containing fluid (e.g., FD&C Yellow 6) to absorb the undesired light components. Other techniques, including ones familiar to those skilled in the art, can also be used.

The distribution of fluid from a fluid reservoir 110 to a cup 120 of a dosing container 100, in some embodiments, is described with reference to FIGS. 1A-6C. As shown in FIGS. 1B and 6C, the container can also include a straw 150, which can be adapted to transport fluid from the reservoir 110 to the cup 120 when the inner volume of the reservoir 110 is pressurized, such as by squeezing the walls of the reservoir 110. The straw 150 can be in fluid communication with a connector 121 of a cup 120. The connector 121, along with other structures of the cup 120 described herein, can provide a fluid pathway into a holding region 122 of the cup 120, which can hold a selected fluid amount before it is removed from the container 100. The location of the connector 121 of the cup 120 can be provided in a number of locations. In some embodiments, the connector 121 can be located off the centerline axis 129 of the cup 120 to allow positioning closer to a slot 160 used to transport fluid into the cup 120, as depicted in FIGS. 6A and 6C.

Though straws of any dimensions suitable can be used with dosing containers as disclosed herein, in some embodiments one or more dimensions of the straw 150 can be adapted to enhance delivery of a selected fluid amount from the reservoir 110 to the cup 120. In one instance, the straw 150 can be adapted with a selected inner diameter to facilitate accurate delivery of fluid to the cup. For example, straws with large inner diameters present a source of error when delivering a selected amount of fluid. When a container 100 is tipped to distribute a selected amount of fluid held in a cup 120, a volume of fluid in the straw 150 may flow into the cup region, thus increasing the actual amount of fluid poured out of the container 100. Accordingly, in some embodiments the inner diameter of the straw can be configured such that one or more of the selected dosages of fluid provided by the container (e.g., transferred into the cup from the reservoir) are within an error of less than about 20%, or about 15%, or about 10%, or about 5%. As well, excessively small inner diameters require more effort to force a fluid through a straw 150. This can provide difficulties for users who have hindered motor skills, who may have difficulty maneuvering a dosage container. Accordingly, some embodiments utilize a straw having a diameter between about 0.08 inches and about 0.1 inches; or between about 0.09 inches and 0.095 inches. Some particular embodiments can utilize a straw with a diameter of about 0.093 inches, for example when delivering doses of about 6 mLs of fluid or greater.

In another instance, the straw 150 can be adapted to extend to nearly the bottom of the reservoir 110, for example to within a distance no greater than about a millimeter. This can help substantially all the volume of fluid in the reservoir 110 to be distributed out of the reservoir 110. As well, it can be advantageous to utilize a straw which does not have excessive length, e.g., longer than necessary to reach the bottom of the reservoir 110, since such length can result in additional volume in a straw that can contribute to errors in the amount of fluid delivered from the container. Accordingly, the length of a straw can be configured to limit the error in a delivered selected fluid amount (e.g., less than about 20%, or about 15%, or about 10%, or about 5%).

Figure 3A:
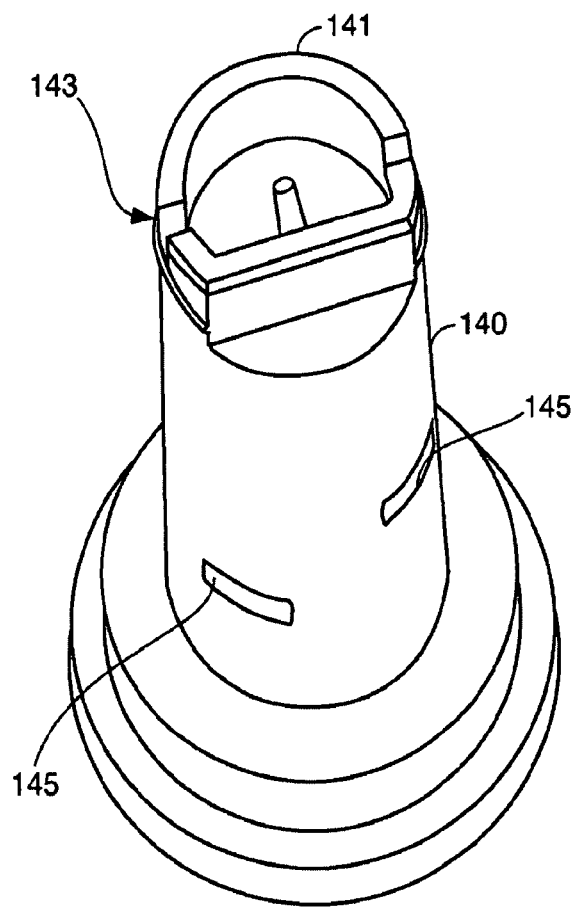
FIG. 3A presents a schematic of a top perspective view of a sleeve used in the dosing container shown in FIG. 1A.
Figure 3B:
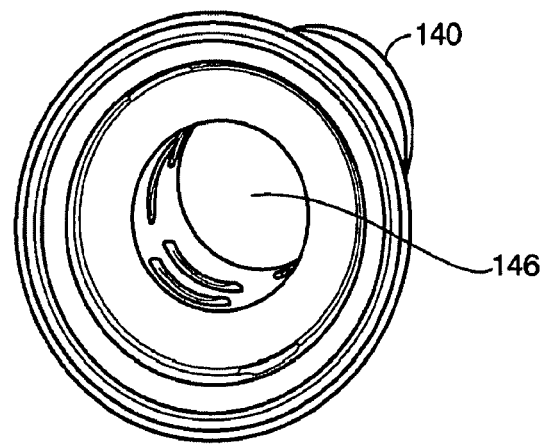
FIG. 3B presents a schematic of a bottom perspective view of a sleeve used in the dosing container shown in FIG. 1A.
Figure 4:
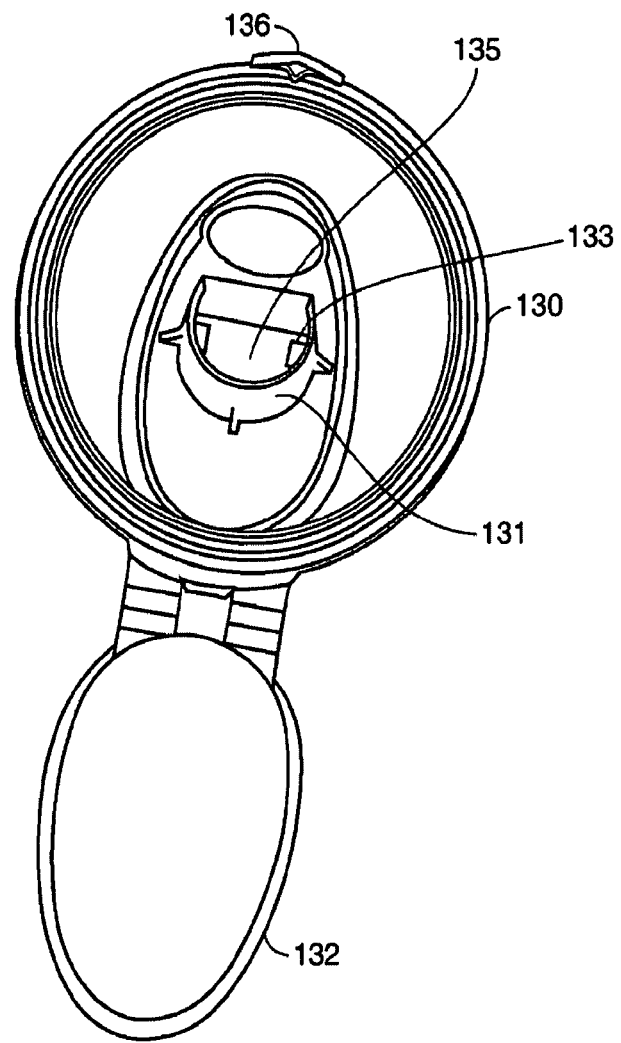
FIG. 4 presents a schematic of a bottom view of a rotatable cap used in the dosing container shown in FIG. 1A.

Consistent with some embodiments, the dosing container 100 can include a sleeve 140 as depicted in FIGS. 2A, 2B, 3A, and 3B. The sleeve can be used in conjunction with a cup and a rotatable cap to select an amount of fluid that is distributed into the cup. In some embodiments, the sleeve can be adapted to couple with the rotatable cap such that the sleeve rotates with the rotatable cap. For example, with reference to FIG. 3A showing a top perspective view of the sleeve 140 and FIG. 4 showing a bottom view of a rotatable cap 130, the raised semicircular structure 141 of sleeve 140 can be adapted to fit within the opening 135 of the rotatable cap 130, with walls 131 adapted to fit around the semicircular structure 141. The protrusions 133 of the rotatable cap can be configured to fit in corresponding slots 143 of the sleeve 140, enhancing rotational coupling between the sleeve 140 and the rotatable cap 130. It is understood, however, that sleeves can be coupled with other portions of a dosing container as well, e.g., the cup.

In general, a sleeve can be adapted to fit over a post structure, with relative movement between the pieces determining a selectable amount of fluid to be transferred. In one exemplary embodiment, a sleeve 140 includes an inner region 146, as exemplified in FIG. 3B, adapted to receive a post structure 125, which can optionally be a portion of a cup 120 as exemplified in FIG. 5. As shown in FIGS. 2A, 2B, and 3A, the sleeve 140 can include one or more openings 145, which can be adapted to provide fluid communication between the inner region 146 of the sleeve 140 and the space outside of the sleeve 140 (e.g., the holding region 122 of the cup 120). When more than one opening is utilized, the openings can be distributed along the length of the sleeve, each opening corresponding with a particular selectable amount of fluid to be deposited into the cup. The openings 145 can also be configured to be distributed around the circumference of the sleeve 140. The position of an opening 145 with respect to the circumference of the sleeve 140 can be chosen to correspond with the selected rotational positions of the rotating cup 130.

As well, the positions can be chosen such that a flip lid 132 does not open in the direction of a user when the container 100 is in a particular orientation.

Figure 5:
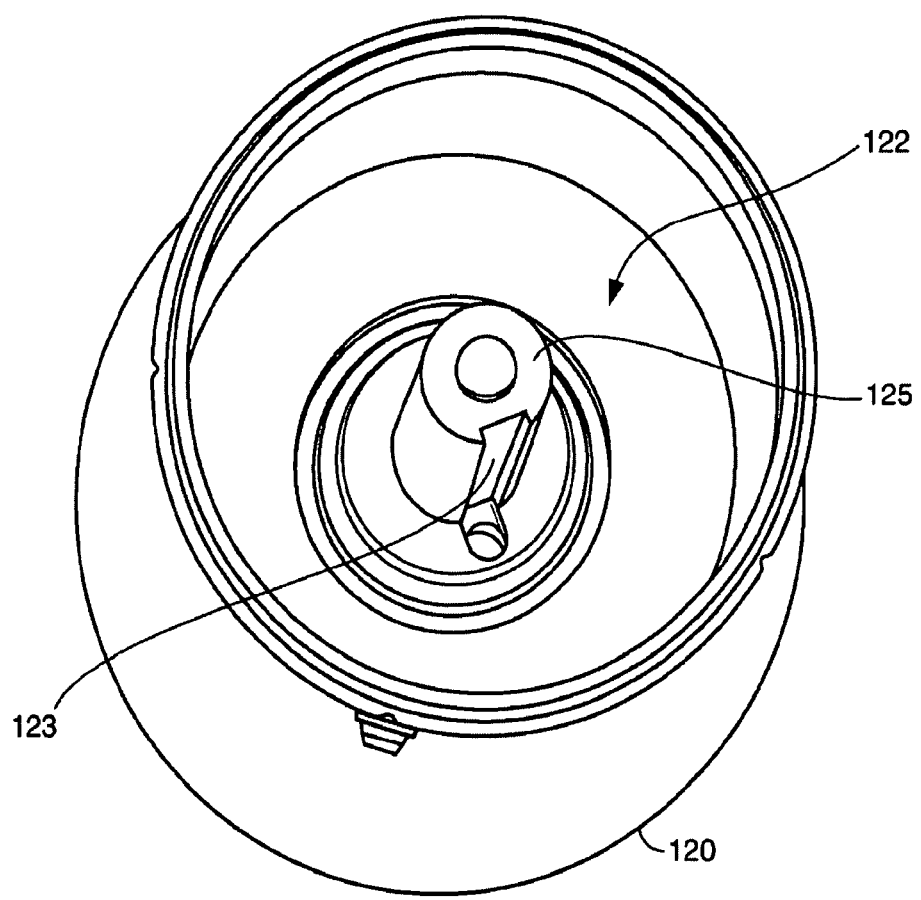
FIG. 5 presents a schematic of a top perspective view of a cup used in the dosing container shown in FIG. 1A.
Figure 6A:
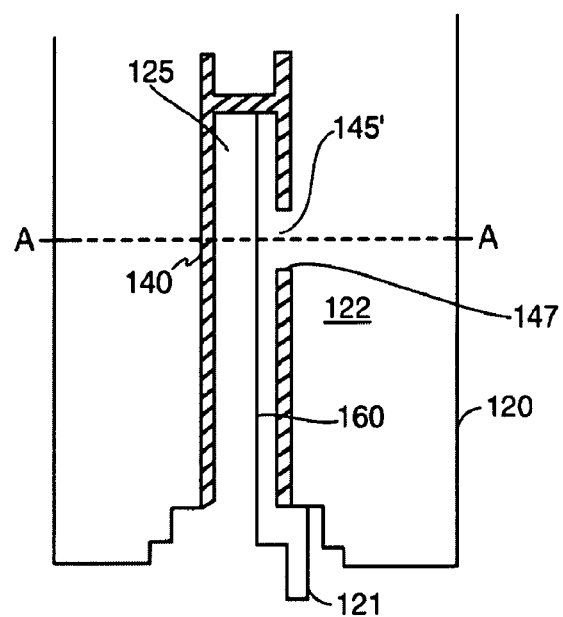
FIG. 6A presents a schematic of a cross-sectional side view of the sleeve coupled with the cup of the dosing container shown in FIG. 1A.
Figure 6B:
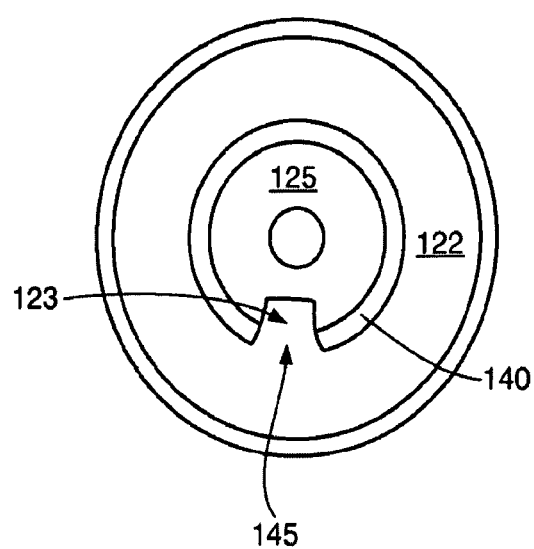
FIG. 6B presents a schematic of a cross-sectional top view of the sleeve coupled with the cup along the A-A line shown in FIG. 6A.
Figure 6C:
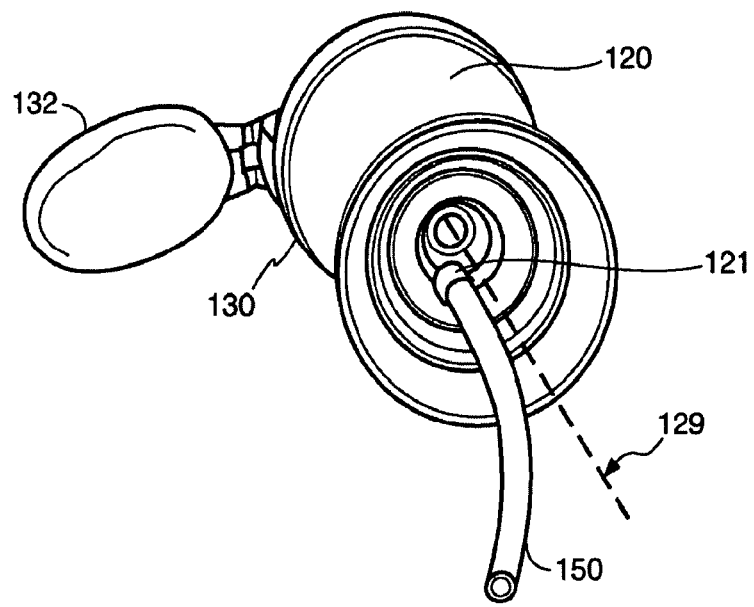
FIG. 6C presents a schematic of a bottom perspective view of a straw, cup, and rotatable top of the dosing container shown in FIG. 1A.

As depicted in FIG. 5, the post structure 125 can include a structure 123 that runs along the length of the post structure 125. The structure 123, exemplified as a groove which does not completely penetrate the post structure 125 in FIG. 5, can form the boundary of a slot 160 when the sleeve 140 is fitted over the post structure 125 as shown in FIG. 6A. The slot 160 can run along the length of the post structure 125, and can provide fluid communication to the connector 121 for a straw 150.

As mentioned earlier, the sleeve 140 can be coupled to rotate with the rotatable cap 130, while the post structure 125 can be adapted to remain fixed, i.e., the rotatable cap 130 rotates relative to the cup 120. Accordingly, to provide a particular selected amount of fluid in the cup 120, the rotatable cap 130 is rotated into a selected position which aligns one designated opening 145' of the sleeve 140 with the slot 160 formed by the groove structure 123 of the post 125 and the wall of the sleeve 140, as depicted by the side cross-sectional view of FIG. 6A and the corresponding upper cross-sectional view of FIG. 6B along the dotted line A-A of FIG. 6A. When fluid is forced up through a straw and into the connector 121, the fluid can continue being guided by the slot 160. Upon reaching the opening 145', fluid can flow through the opening 145' and into the holding region 122 of the cup 120. Fluid can continue to flow and accumulate in the holding region 122 until the liquid level exceeds the height of lower lip 147 of the opening 145'. When the fluid level in the holding region 122 exceeds the height of lower lip 147, fluid in the holding region 122 will tend to flow back through the slot 160 and into the reservoir 110 until the level in the holding region 122 is substantially equal to the level of the lower lip 147. Thus, the position of the opening 145' can determine the amount of fluid deposited into the cup. In substantially similar fashion, other openings when aligned with the groove 123 can determine other amounts of fluid depending upon their location along the length of the sleeve 140. Accordingly, the rotatable cap 130 and sleeve 140 can be adapted with openings 145 of the sleeve 140 each corresponding to a selected rotatable cap position that is associated with a desired amount of fluid to be deposited into the cup 120 from the reservoir 110.

Figure 7A:
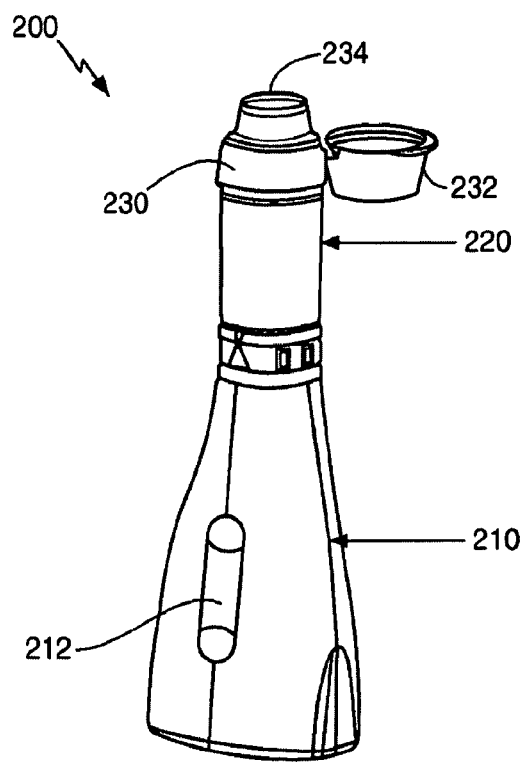
FIG. 7A presents a schematic of a perspective view of another dosing container consistent with some embodiments of the invention.
Figure 7B:
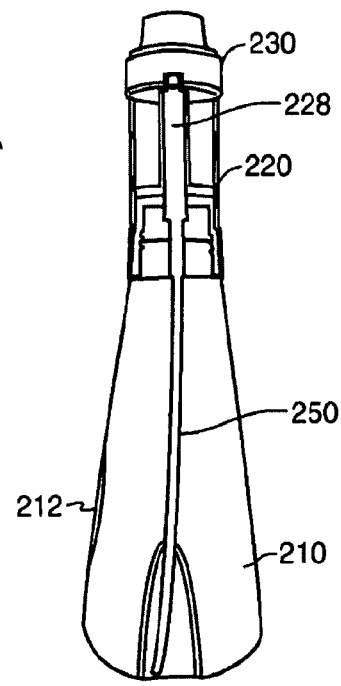
FIG. 7B presents a schematic of a cross-sectional view of the dosing container shown in FIG. 7A.

The previous description of the interworkings of a dosing container's reservoir 110, cup 120, sleeve 140, and rotatable cap 130 to deliver fluid provides just one exemplary mechanism for fluid delivery. Many variations of one or more elements can also be employed within the scope of the present invention. Some of these variations are discussed in another exemplary dosing container depicted in FIGS. 7A-7F, according to some embodiments. As shown in FIGS. 7A and 7B, a dosing container 200 includes a reservoir 210, a cup 220, and a rotatable cap 230. The reservoir 210 can include an indentation 212, which can provide an orientation to the dosing container 200. The rotatable cap 230 includes a flip lid 232, which can snap shut to cover the opening 234 from which fluid can be removed. Accordingly, a dosing container consistent with these embodiments can optionally include the orientation features and advantages discussed with respect to the dosing container 100 shown in FIGS. 1A-6C.

Figure 7C:
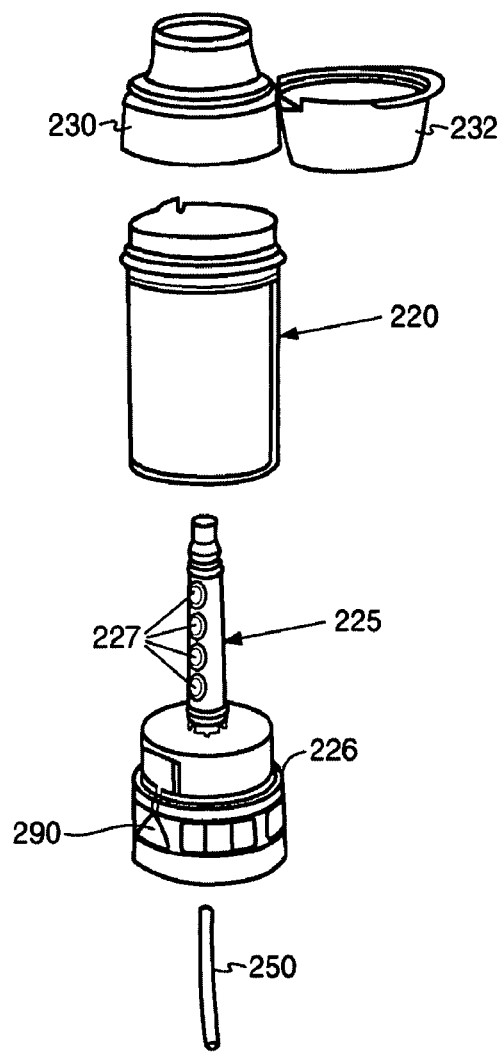
FIG. 7C presents a schematic a exploded view of some pieces of the dosing container shown in FIG. 7A.

With reference to FIGS. 7B and 7C, the rotatable cap 230 can be coupled to the cup 220 in a manner such that the cap 230 and cup 220 move together, i.e., the cup 220 is rotatable, unlike cups utilized in other embodiments described herein. Such an embodiment can be advantageous for persons with limited hand motor skills since a larger structure (e.g., cap and cup ensemble) can be gripped and rotated to determine a selected amount of fluid to be distributed.

Figure 7D:
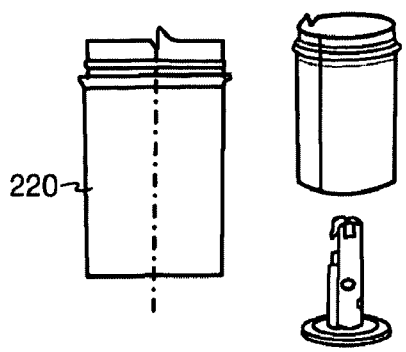
FIG. 7D presents a schematic showing views of a cup used in the dosing container shown in FIG. 7A.
Figure 7E:
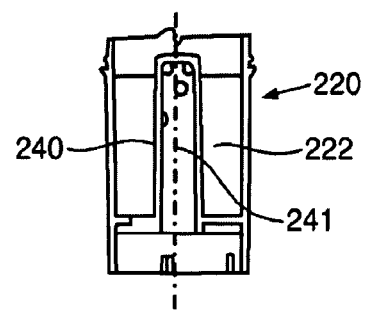
FIG. 7E presents a schematic of a cross-sectional side view of the cup shown in FIG. 7D.
Figure 7F:
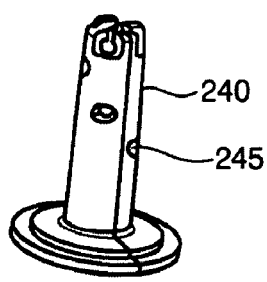
FIG. 7F presents a schematic perspective view a post structure shown in FIG. 7D.

As depicted in FIGS. 7D and 7E, the cup 220 of these embodiments can be integrated with a sleeve 240. The cup 220 includes a fluid holding region 222 in which selected amounts of fluid can be held. As shown in FIG. 7F, the sleeve 240 can include one or more openings 245 that each penetrate the sleeve 240 to an inner hollow region 241. The openings 245 can be distributed along the length of the sleeve 240. The inner hollow region 241 of the sleeve 240 can be adapted to accept a post structure 225, i.e., the sleeve 240 of the cup 220 can fit over the post structure 225 shown in FIG. 7C. The post structure 225 is coupled to a connector 226, which is adapted to couple to the reservoir 210 in a fixed manner, i.e., upon coupling the connector 226 and the reservoir 210, the connector 226 and post structure 225 do not rotate during fluid distribution of the dosing container 200. The post structure 225 can include one or more openings 227. The openings 227 can be adapted to penetrate the post structure 225 to an inner region 228. The inner region 228 forms a fluid pathway along the centerline of the post structure 225, which is in communication with a straw 250. The straw 250 can provide a fluid pathway from the reservoir 210 to the inner region 228 in the post structure 225. The connector 226 can optionally include a marker or indicator 290, to help identify a selected position that the rotatable cap 230 and cup 220 are rotated to. Markings and indicators can also be included on the cup 220 or cap 230.

Delivery of a selected fluid amount from the reservoir 210 to the cup 220 of dosing container 200 can be achieved as follows. A user can rotate the cap 230 and cup 220 together into a selected position. The sleeve 240 rotates with the cup 220, and can be adapted such that one of the openings 245 of the sleeve 240 rotates into alignment with an opening 227 of the post structure 225. Accordingly, a fluid pathway, connecting the reservoir 210 and holding region 222 of the cup 220, is established through the straw 250, into the inner region 228 of the post structure 225, and through the openings 227, 245 of the post structure 225 and sleeve 240. Pressurization of the reservoir 210, e.g., squeezing the walls of the reservoir 210, can drive fluid along the fluid pathway and into the holding region 222 of the cup. As analogously described earlier with respect to the dosing container 100 depicted in FIGS. 1A-6C, when the fluid level in the cup 220 exceeds the height of the opening 227 of the sleeve 240 corresponding with the selected fluid amount, fluid will flow back into the reservoir 210 until the fluid height in the cup is substantially the same as the lower lip of the opening 227 corresponding with the selected fluid amount.

It is appreciated that variations of the dosing container 200 are within the scope of some embodiments described herein. For example, the use of openings 227 in a post structure 225, or openings 245 in a sleeve 240 can be replaced with other structures that can perform similar functions, such as the use of a penetrating slot to replace the openings. The alignment of the slot with the openings of the other structure can define a fluid pathway between the cup 220 and the reservoir 210 in which fluid can flow. Other similar structures, including those known to one skilled in the art, can also be incorporated in some embodiments.

It is also understood that though embodiments consistent with the dosing containers depicted in FIGS. 7A-7F show some features that are not present in the dosing container depicted in FIGS. 1A-6C and visa versa, many features described with respect to one dosing container can be utilized with respect to another. In one example, a dosing container consistent with that depicted in FIGS. 7A-7F can utilize a sleeve and post that are structured like the sleeve and post depicted in FIGS. 1A-6C, albeit with the sleeve still coupled to a rotatable cup and the post still coupled to a connector for attachment to the reservoir. In another example, a dosing container consistent with FIGS. 1A-6C can utilize a sleeve and post structure with openings as depicted in FIGS. 7A-7F, though maintaining the sleeve coupled to the rotatable cap and the post structure integrated with a fixed cup. Other examples include features regarding the straw; markings to help orient the container relative to a user or a rotating element relative to a non-rotating element; sizes of dosing container pieces; the amount of fluid distributed by the containers; types of fluid that can be distributed; and others can be equally utilized with either described dosing container, or other dosing containers not explicitly described herein. All these variations are within the scope of the present invention.

Beyond the features already disclosed herein, dosing containers can also include additional features which can facilitate their use in dispensing a fluid drug. Though the dosing containers disclosed herein can have their reservoirs filled multiple times, in some embodiments the dosing container can be adapted to be a disposable device, i.e., the container is designed to be disposed after the delivery of all fluid in the reservoir. Accordingly, the container can be constructed of relatively inexpensive materials such as plastics (e.g., polypropylene) and other extrudable materials that can be formed into particular shaped pieces. In some instances, dyes can be added to color the bottle.

Furthermore, when a dosing bottle is designed to hold a fluid-drug that degrades relatively quickly in fluid form relative to solid form, it can be beneficial to distribute the dosing bottle with the drug in solid form for dispersal into a fluid form at a later time. The dosing bottle can be distributed in separate pieces for assembly just prior to dispersal of the solid drug into a fluid, followed by insertion of the fluid-drug into a reservoir of a dosing bottle. Accordingly, some embodiments of a dosing container include additional features tailored for use in such an instance. In one example, as depicted in FIG. 2A, a dosing bottle can be distributed in separate pieces such as a reservoir 110, a cup 120, a sleeve 140, a rotatable cap 130, and a straw (not shown). The reservoir 110 can include threading to accept cup 120. The threading can be any standard threading, but can also be threading consistent with a standard child-proof cap. Such threading can help safeguard the fluid within the reservoir from tampering upon insertion in to the container.

Alternatively, the threading of the reservoir 110 and cup 120 can be adapted such that upon be coupled together, the reservoir 110 and cup 120 are coupled together such that they are intended not to be separated. This threading can be advantageously utilized in disposable bottles intended to hold only one reservoir of fluid, thus providing additional safeguarding of the fluid from tampering or accidental usage. Such intended permanent coupling can also be utilized advantageously between the sleeve 140, the cup 120 and the rotatable cap 130, though the cap 130 is intended to maintain the ability to rotate relative to the cup 120 in some embodiments. It is also understood that child-proof threading, threading intended to maintain a permanent coupling, or other types of threading (e.g., standard threading to allow pieces to the twisted together and apart) can be utilized with various pieces of any dosing container, such as the container 200 depicted in FIGS. 7A-7F.

Packaging and Delivery of a Fluid Drug

Some embodiments are directed to kits that can include a dosing container to treat persons with decreased motor functioning skills. One exemplary kit is directed to treating a person with Parkinson's Disease (herein "PD"). The kit can include a container that is adapted to deliver at least one selected amount of fluid. The kit can also include a concentrated carbidopa formulation and a concentrated levodopa formulation. The formulations can be in liquid or solid form, and can be mixed together or kept in separate packages. Embodiments that utilize powdered formulations of carbidopa and/or levodopa can be advantageous since the activity of carbidopa and levodopa is generally preserved for a longer period of time when the material is in solid form.

In some embodiments, the concentrated formulations can be adapted to provide one or more dosages of fluid-drug for treating a patient with PD when the formulations are dispersed in water. For instance, the dispersed concentrated formulations can form a fluid drug consistent with a carbidopa and/or levodopa containing fluid as described in U.S. Patent Application Publication No. US 2005/0203185 A1, bearing Ser. No. 11/083,168; or U.S. Patent Application Publication No. US 2005/0070608 A1, bearing Ser. No. 10/926,702. For example, a fluid formulation having a carbidopa to levodopa ratio of about 1:4.

A container that can be included in a kit includes any type of dosing container which can be used to distribute a fluid drug, such as the ones disclosed in the present application. In particular, the dosing container can be disassembled to some degree in the kit. Such a kit can advantageously facilitate distribution of a degradable fluid drug in the marketplace. For example, the kit can include a dosing bottle disassembled into pieces as shown in FIG. 2A, which also includes concentrated formulations of carbidopa and levodopa. The kit can be distributed to a pharmacist from a manufacturer. Subsequently, the pharmacist can disperse the concentrated formulations in water, and add other materials as necessary, to produce a properly formulated fluid-drug. The fluid-drug can be placed into the reservoir 110, and the container 100 can be sealed. This ensemble can then be distributed to a individual consumer, such as a PD patient. When the dosing container 100 includes features such as being disposable and/or being sealed so that the reservoir cannot be accessed, tampering of the fluid drug can be hindered, and an added degree of consumer safety can be achieved.

In related embodiments, a kit can include a plurality of dosage containers that are each adapted to deliver selected dosages of fluid. As well, a plurality of concentrated formulations of carbidopa and levodopa can be included. In one embodiment, pieces of the kit are packaged such that an equal number of containers, concentrated formulations of carbidopa, and concentrated formulations of levodopa. The containers and concentrated formulations can include any number of the features previously discussed above. Such a kit of multiple containers and formulations can help facilitate distribution of a carbidopa/levodopa fluid drug in the marketplace. The kits can be packaged in any manner that is convenient, such as placing individually wrapped formulations within a reservoir of a container.

It is readily appreciated that these kits can be modified while staying within the scope of the present invention. Indeed, different types of drug formulations can be utilized beyond carbidopa or levodopa, such as other formulations for treating PD. As well, kits can be assembled that treat other types of disorders such as motor skill disorders beyond PD. All these modifications, including ones understood by those skilled in the art, are contemplated herein.

Other embodiments are directed to methods of providing a drug for treating a disorder such as Parkinson's Disease or other type of motor disorder. The method can include providing one or more formulations, e.g., concentrated, that include carbidopa and levodopa. The formulation can be dispersed in water. The dispersed formulation can be contained in a dosing container. The dosing container can be adapted to provide selected dosages of the dispersed formulation. Any of the dosing containers disclosed in the present application can be utilized, with any number of the features disclosed herein. In one example, the container is adapted to be operated by a patient having hindered fingertip motor skills. In another example, the dosing container can be adapted to lock the container after the dispersed formulation is inserted into the container, e.g., the pieces of a container are designed to be inseparable after assembly; this can help reduce potential tampering and contamination of the dispersed formulation. In yet another example, the dosing container can be adapted to displace a selected dosage of dispersed formulation by squeezing the container while the container is in an upright orientation. Such squeezing can displace the selected dosage from a reservoir section to a cup section of the dosing container. It is apparent that modification to these methods using any of the features of devices disclosed in the present application are well within scope of the present invention.

One skilled in the art will appreciate further features and advantages of the invention based on the above-described embodiments. Accordingly, the invention is not to be limited by what has been particularly shown and described, except as indicated by the appended claims. Indeed, as previously mentioned, any number of the features of devices and methods disclosed herein can be combined in any variation and order to produce embodiments of the present invention. All publications and references cited herein are expressly incorporated herein by reference in their entirety.

What is claimed is:

1. A dosing container operable by a person with limited hand motor skills, comprising:
   a reservoir for holding a fluid;
   a cup adapted to be coupled to the reservoir for holding at least one or more than one selected dosage of the fluid; and
   a rotatable cap adapted to be coupled to the cup, the rotatable cap further adapted to rotate to at least one selected position for distributing an amount of fluid corresponding with the at least one selected dosage of the fluid, the rotatable cap adapted to be hand-grippable and rotated by a person with hindered fingertip motor skills;
   wherein the rotatable cap is coupled to the cup in a manner such that the rotatable cap and cup move together, that is, the cup is rotatable; and
   wherein the fluid comprises carbidopa and levodopa dispersed in a medium such as water.

2. The dosing container of claim 1, wherein the reservoir includes at least one indentation for orienting the container in a particular direction relative to the person operating the dosing container.

3. The dosing container of claim 2, wherein the dosing container is adapted to fill the cup with the selected dosage of fluid when the dosing container is squeezed by the person.

4. The dosing container of claim 2, wherein the rotatable cap includes a flip lid, and the flip lid opens in a direction away from the person when the container is oriented in the particular direction.

5. The dosing container of claim 1, wherein the reservoir is adapted to hinder exposure of the fluid to a light capable of inducing degradation in at least one of carbidopa and levodopa dispersed in the fluid.

6. The dosing container of claim 1, further comprising a straw
   adapted to be fitted to a portion of the cup for drawing fluid from the reservoir to the cup, the straw having an inner diameter sized to provide the selected dosages of fluid within an error of about 10%.

7. The dosing container of claim 1, further comprising a sleeve adapted to couple and rotate with the rotatable top, and
   wherein the sleeve includes at least one opening along a length, and each opening corresponds to at least one selected dosage, and
   wherein the sleeve further is adapted to fit over a post structure of the cup, and the post structure and fitted sleeve form a slot for guiding fluid from the reservoir into the cup.

8. The dosing container of claim 7, further comprising a straw
   for drawing fluid from the reservoir to the cup, the straw adapted to be fitted to the cup in a position away from an axial centerline of the cup.

9. A kit for treating Parkinson's Disease, comprising:
   a container adapted to deliver at least one selected amount of fluid;
   a concentrated carbidopa formulation; and
   a concentrated levodopa formulation,
   the concentrated carbidopa formulation and the concentrated levodopa formulation adapted to provide at least one dosage of fluid-drug for treating a patient with Parkinson's disease when the formulations are dispersed in water.

10. The kit of claim 9, wherein at least one of the concentrated carbidopa formulation and levodopa formulation is a powdered formulation.

11. The kit of claim 9, wherein the concentrated carbidopa formulation and concentrated levodopa formulation comprise a ratio of carbidopa to levodopa of about 1:4.

12. The kit of claim 9, wherein the container comprises:
    a reservoir for holding a fluid having the concentrated carbidopa formulation and the concentrated levodopa formulation; and
    a rotatable cap adapted to be coupled to the reservoir, the rotatable cap further adapted to rotate to at least one selected position for distributing the at least one selected amount of fluid corresponding with the at least one or more than one dosage of fluid-drug, the rotatable cap adapted to be hand-grippable and rotated by a person with hindered fingertip motor skills.

13. The kit of claim 12, wherein the reservoir and rotatable cap are adapted to hinder decoupling after the reservoir and rotatable cap are coupled together.

14. The kit of claim 9, further comprising:
    a plurality of containers adapted to deliver selected dosages of liquid;
    a plurality of concentrated carbidopa formulations; and
    a plurality of concentrated levodopa formulations.

15. A method of providing a drug for treating Parkinson's Disease, comprising: providing at least one powdered formulation comprising carbidopa and levodopa; dispersing the carbidopa and levodopa in water; and containing the dispersed carbidopa and levodopa in a dosing container of claim 1.

16. The method of claim 15, further comprising:
    locking the container after the container is closed with the dispersed carbidopa and levodopa to hinder tampering.

* * * * *